(12) United States Patent
Reynolds

(10) Patent No.: US 12,582,414 B2
(45) Date of Patent: Mar. 24, 2026

(54) DEVICES AND METHODS FOR REMOVING BONE

(71) Applicant: WRIGHT MEDICAL TECHNOLOGY, INC., Memphis, TN (US)

(72) Inventor: David G. Reynolds, Fairport, NY (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 876 days.

(21) Appl. No.: 17/904,017

(22) PCT Filed: Apr. 7, 2021

(86) PCT No.: PCT/US2021/070358
§ 371 (c)(1),
(2) Date: Aug. 11, 2022

(87) PCT Pub. No.: WO2021/207757
PCT Pub. Date: Oct. 14, 2021

(65) Prior Publication Data
US 2023/0157705 A1 May 25, 2023

Related U.S. Application Data

(60) Provisional application No. 63/008,109, filed on Apr. 10, 2020.

(51) Int. Cl.
*A61B 17/16* (2006.01)
*A61B 17/17* (2006.01)

(52) U.S. Cl.
CPC .......... *A61B 17/1615* (2013.01); *A61B 17/17* (2013.01)

(58) Field of Classification Search
CPC .. A61B 17/1615; A61B 17/17; A61B 17/1617
See application file for complete search history.

(56) References Cited

U.S. PATENT DOCUMENTS 5,768,134 A 6/1998 Swaelens et al.
6,482,209 B1 11/2002 Engh et al.
(Continued)

FOREIGN PATENT DOCUMENTS

AU 2004201725 B2 7/2007
CA 2490673 C * 11/2011 ........... A61F 2/3603
(Continued)

OTHER PUBLICATIONS

International Search Report and Written Opinion issued in connection with International Patent Application No. PCT/US2021/070358, Oct. 20, 2021, 17 pages.

*Primary Examiner* — Kevin T Truong
*Assistant Examiner* — Diana Jones
(74) *Attorney, Agent, or Firm* — DUANE MORRIS LLP

(57) ABSTRACT

A system or kit includes a rotating tool and a guide. The rotating tool includes an elongated shaft with at least one cutting edge. The rotating tool is configured to remove bone from a patient. The guide includes a body comprising a contact surface and a guide channel. The contact surface is configured to position the guide relative to a patient or an implant. The guide channel is configured to receive the elongated shaft and to allow the cutting edge to be swept along a path. The path corresponds to a portion of the bone to be removed. A method of removing an implant includes forming an incision in a patient. The method further includes inserting a rotating tool into the incision such that a cutting edge of the rotating tool is adjacent to a surface of the implant. The method further includes sweeping the cutting (Continued)

edge along a first path adjacent to the surface of the implant to remove bone adjacent to the implant.

16 Claims, 16 Drawing Sheets

(56) References Cited

U.S. PATENT DOCUMENTS

| | | | |
|---|---|---|---|
| 7,163,542 B2 * | 1/2007 | Ryan ................. | A61B 17/1617 |
| | | | 606/96 |
| 9,017,334 B2 | 4/2015 | Carroll et al. | |
| 9,402,640 B2 | 8/2016 | Boileau et al. | |
| 10,105,151 B2 | 10/2018 | Reynolds et al. | |
| 2006/0122616 A1 * | 6/2006 | Bennett .............. | A61B 17/1764 |
| | | | 606/87 |
| 2011/0009977 A1 * | 1/2011 | Fridshtand ......... | A61F 2/30767 |
| | | | 623/23.35 |
| 2018/0014891 A1 | 1/2018 | Krebs et al. | |
| 2018/0263782 A1 | 9/2018 | Lang et al. | |
| 2018/0317942 A1 * | 11/2018 | Awtrey ............. | A61B 17/1796 |
| 2019/0069940 A1 | 3/2019 | Winnen | |

FOREIGN PATENT DOCUMENTS

| | | | | |
|---|---|---|---|---|
| JP | 2005526524 A | 9/2005 | | |
| WO | 2019009891 A1 | 1/2019 | | |
| WO | WO-2019245867 A1 * | 12/2019 | ............. | A61B 34/25 |

* cited by examiner

DEVICES AND METHODS FOR REMOVING BONE

CROSS-REFERENCE TO RELATED APPLICATIONS

This application is a National Stage Application, filed under 35 U.S.C. 371, of International Patent Application No. PCT/US2021/070358, filed on Apr. 7, 2021, which claims priority to U.S. Provisional Application No. 63/008,109, filed on Apr. 10, 2020, the entireties of which are is incorporated by reference herein in its entireties.

BACKGROUND

An ankle joint may become severely damaged and painful due to arthritis, prior ankle surgery, bone fracture, osteoarthritis, and/or one or more additional conditions. Options for treating the injured ankle have included anti-inflammatory and pain medications, braces, physical therapy, joint arthrodesis, and total ankle replacement.

Total ankle replacement generally comprises at least two components-a tibial implant and a talar implant. The implants comprise articulation surfaces sized and configured to mimic the range of motion of the ankle joint. For example, the talar implant may comprise an implant sized and configured to mimic the talar dome and the tibial implant may comprise an articulation surface sized and configured to mimic articulation of the tibia.

There are times when a portion of the implant (e.g., the tibial implant) needs to be removed and replaced. For example, in some patients, the tibial implant may need to be removed to allow for the replacement with a larger or alternative implant. When removing a tibial implant, bone may need to be removed from around the stem of the implant to allow the stem to be removed from the tibia.

SUMMARY

In one aspect, a burr for removing bone includes an elongated shaft and a depth stop. The elongated shaft has at least one cutting edge. The depth stop is coupled to the elongated shaft and extends outward from the elongated shaft. The depth stop is configured to contact tissue of a patient or a burr guide to restrict a depth of insertion of the elongated shaft.

In another aspect, a burr guide includes a body having a contact surface configured to contact tissue of a patient and a first guide channel. The first guide channel is configured to guide the burr as the burr is swept along a path, the path corresponding to a portion of bone to be removed.

In another aspect, a system includes a burr and a burr guide. The burr includes an elongated shaft with at least one cutting edge. The burr is configured to remove bone from a patient. The burr guide includes a body comprising a contact surface and a guide channel. The contact surface is configured to contact tissue of a patient. The guide channel is configured to receive the burr and to allow the burr to be swept along a path. The path corresponds to a portion of the bone to be removed.

In another aspect, a method of removing an implant includes forming a bore in a bone of a patient. The method further includes inserting a burr through the bore such that the burr is adjacent a surface of the implant. The method further includes sweeping the burr along a first path adjacent to the surface of the implant to remove bone adjacent to the implant.

In another aspect, an implant includes a stem configured to be inserted into a recess in a bone. The stem has a first face, which may be a lateral face that is substantially planar, and a second face, which may be a medial face that is substantially planar. The first face and the second face may be inclined relative to one another about a first axis.

In another aspect, a method of planning removal of an implant from a patient is provided. The method includes receiving at least one image of the implant in the patient. The method further includes identifying regions of trabecular bone, cortical bone, and bone void. The method further includes determining one or more paths for translation of a burr along the implant to remove bone adjacent to the implant. The paths are configured to remove sufficient bone to allow removal of the implant while minimizing removal of cortical bone.

BRIEF DESCRIPTION OF THE DRAWINGS

These and other features and advantages of the apparatuses and methods described herein will be more fully disclosed in, or rendered obvious by, the following detailed description of the preferred embodiments, which is to be considered together with the accompanying drawings wherein like numbers refer to like parts.

DETAILED DESCRIPTION

Figure 1:
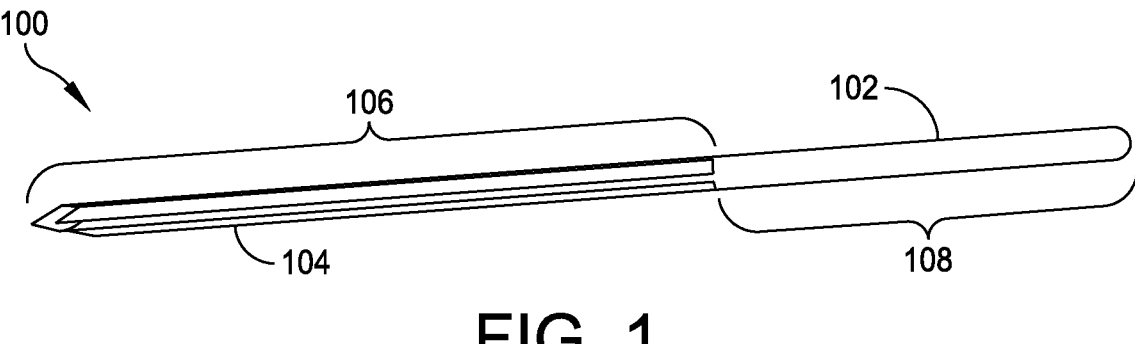
FIG. 1 is a perspective view of one example of a burr in accordance with some embodiments.

This description of preferred embodiments is intended to be read in connection with the accompanying drawings, which are to be considered part of the entire written description of this invention. The drawing figures are not necessarily to scale and certain features of the invention may be shown exaggerated in scale or in somewhat schematic form in the interest of clarity and conciseness. In the description, relative terms such as "horizontal," "vertical," "up," "down," "top," and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

The devices, systems, and methods described herein provide for the removal of bone to ease removal of an implant from a bone or, alternatively, to prepare a bone for implantation of an implant. The systems include burrs that are configured to be swept along a path to remove a desired portion of bone. This disclosure further describes guides for such burrs and implants with stems designed to fit within cavities prepared by sweeping a burr within a bone.

FIGS. 1-4 show multiple embodiments of a rotating cutting tool, e.g., a burr, which can be included in a kit or system for removing an implant or preparing a bone for an implant and used in the methods described herein. Burrs advantageously can turn tight corners, follow along planes, and/or be used to sweep arcs (e.g., cylindrical or conical surfaces). FIG. 1 shows one example of a burr 100 having an elongated shaft 102 with at least one cutting edge 104. In various embodiments, the burr 100 can include one, two, three, or more cutting edges 104. The cutting edges 104 can be straight (i.e., extending axially along the elongated shaft 102) or helical. The elongated shaft 102 includes a cutting portion 106 along which the cutting edges 104 extend and a non-cutting portion 108 that does not contain a cutting edge. The non-cutting portion 108 preserves bone from being cut and maintains the access point as intact as possible.

Figure 2:
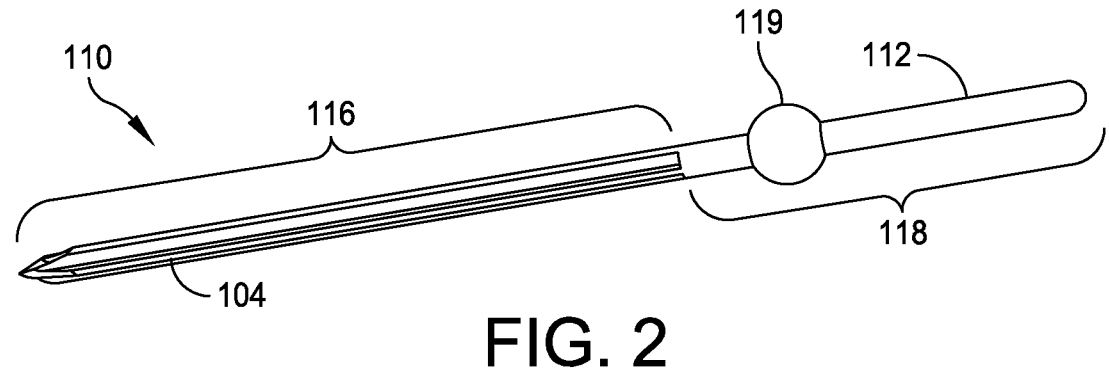
FIG. 2 is a perspective view of another example of a burr in accordance with some embodiments.

FIG. 2 shows another embodiment of a burr 110. The burr 110 has an elongated shaft 112 with at least one cutting edge 114. In various embodiments, the burr 110 can include one, two, three, or more cutting edges 114. The cutting edges 114 can be straight (i.e., extending axially along the elongated shaft 112) or helical. The elongated shaft 112 includes a cutting portion 116 along which the cutting edges 114 extend and a non-cutting portion 118 that does not contain a cutting edge. The burr 110 further includes a depth stop 119 coupled to the elongated shaft 102. The depth stop 119 extends outward from the elongated shaft 112 and is configured to contact tissue of a patient or a surface of a burr guide to restrict a depth of insertion of the elongated shaft 112, as described further herein. The depth stop 119 extends from the non-cutting portion 118 of the elongated shaft 112. As shown in FIG. 2, the depth stop 119 can be in the form of a sphere, although one of ordinary skill in the art will understand that the depth stop 119 can have other shapes or forms. For example, the depth stop 119 may be in the form of a truncated code or rectangular or a squared shoulder to list only a few possibilities.

Figure 3:
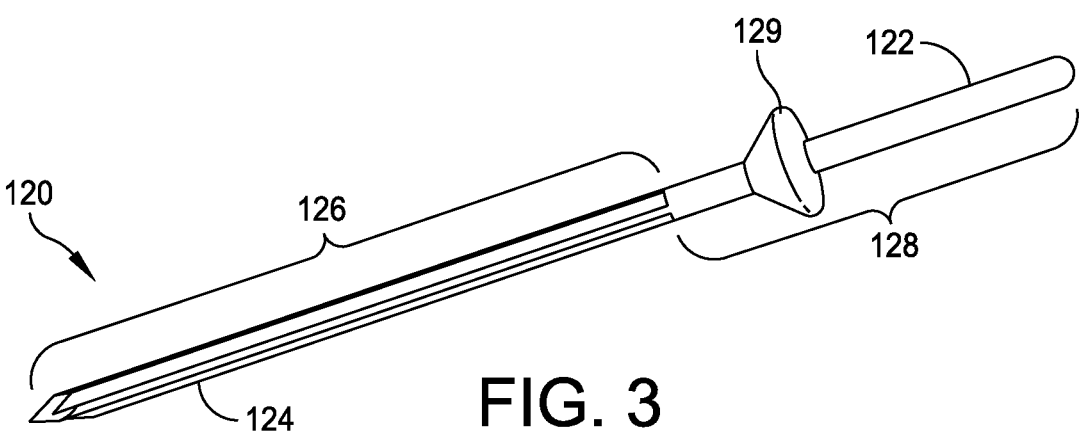
FIG. 3 is a perspective view of another example of a burr in accordance with some embodiments.

Another embodiment of a burr 120 is shown in FIG. 3. The burr 120 has an elongated shaft 122 with at least one cutting edge 124. In various embodiments, the burr 120 can include one, two, three, or more cutting edges 124. The cutting edges 124 can be straight (i.e., extending axially along the elongated shaft 122) or helical. The elongated shaft 122 includes a cutting portion 126 along which the cutting edges 124 extend and a non-cutting portion 128 that does not contain a cutting edge. The burr 120 further includes a depth stop 129 coupled to the elongated shaft 122. The depth stop 129 extends outward from the elongated shaft 122 and is configured to contact tissue of a patient or a surface of a burr guide to restrict a depth of insertion of the elongated shaft 122, as described further herein. The depth stop 129 extends from the non-cutting portion 128 of the elongated shaft 122. As shown in FIG. 3, the depth stop 129 is in the form of a truncated cone.

Figure 4:
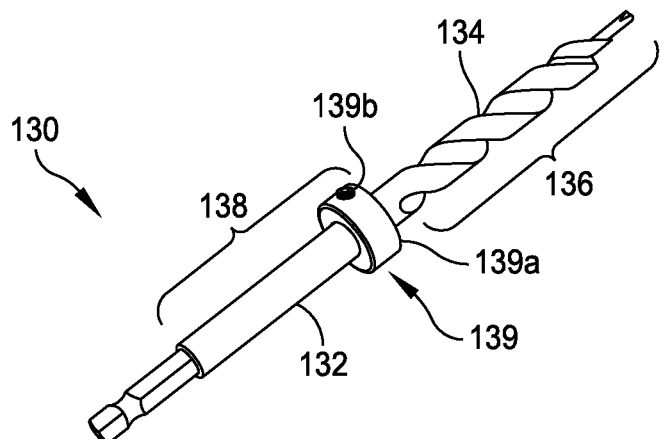
FIG. 4 is a perspective view of another example of a burr in accordance with some embodiments.

Another example of a burr 130 in accordance with some embodiments is shown in FIG. 4. The burr 130 has an elongated shaft 132 with at least one cutting edge 134. In various embodiments, the burr 130 can include one, two, three, or more cutting edges 134. The cutting edges 134 can be straight (i.e., extending axially along the elongated shaft 132) or helical (as shown in FIG. 4). The elongated shaft 132 includes a cutting portion 136 along which the cutting edges 134 extend and a non-cutting portion 138 that does not contain a cutting edge. The burr 130 further includes a depth stop 139 coupled to the elongated shaft 132. The depth stop 139 extends outward from the elongated shaft 132 and is configured to contact tissue of a patient or a surface of a burr guide to restrict a depth of insertion of the elongated shaft 132, as described further herein. The depth stop 139 extends from the non-cutting portion 138 of the elongated shaft 132.

In the embodiment of FIG. 4, the depth stop 139 includes a collar 139a that is adjustable along the length of the elongated shaft 132. The depth stop 139 can further include a set screw 139b engaged with the collar 139a such that rotation of the set screw 139b secures the collar 139a in position along the elongated shaft 132.

In some embodiments, the elongated shaft 132 includes a plurality of stops along the length of the elongated shaft 132. In such embodiments, the depth stop 139 is configured to engage one of the stops to locate the depth stop 139 along the elongated shaft 132.

Figure 5:
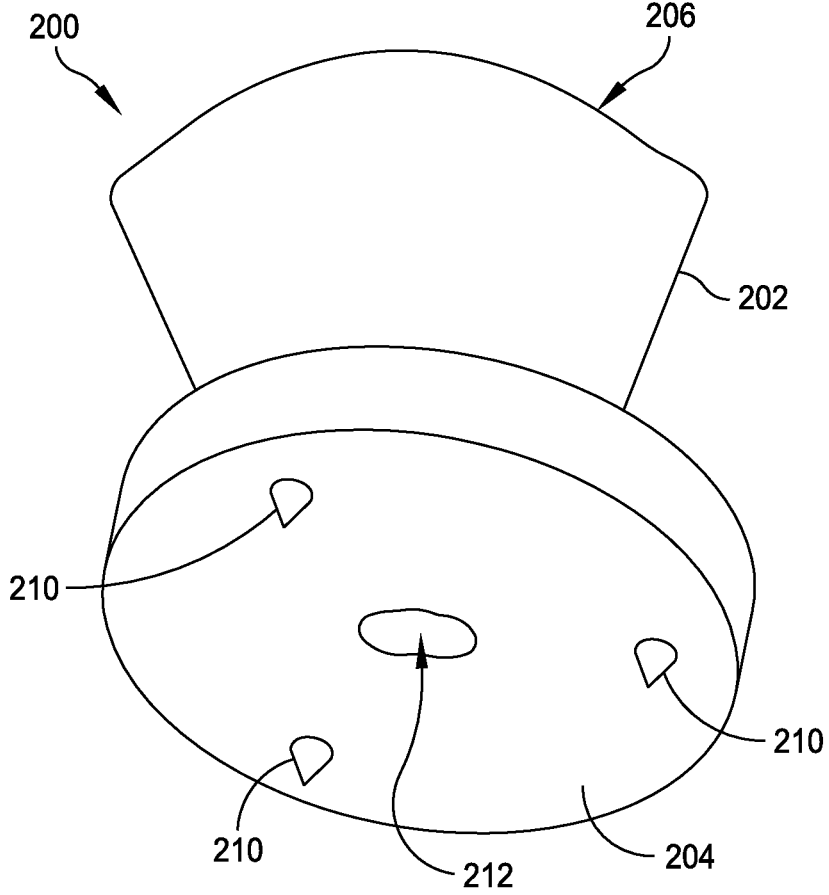
FIG. 5 is a bottom perspective view of one example of a burr guide in accordance with some embodiments.
Figure 6:
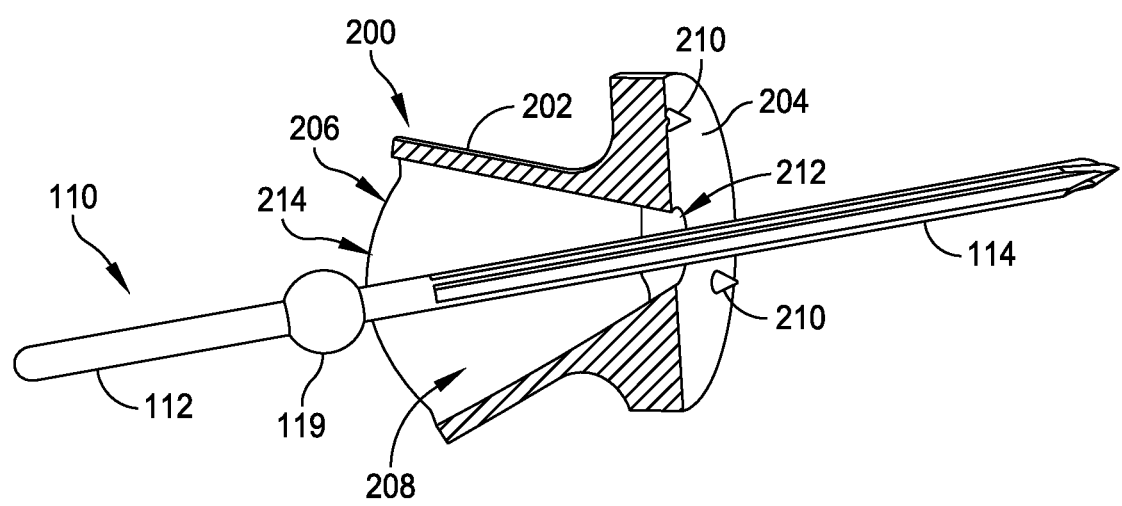
FIG. 6 is a partial cross-sectional perspective view of a system including a burr, such as the burr illustrated in FIG. 2, and a burr guide, such as the burr guide illustrated in FIG. 5, in accordance with some embodiments.
Figure 8:
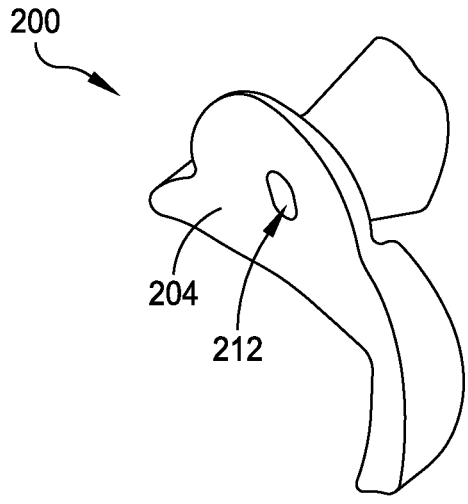
FIG. 8 is a perspective view of one example of a burr guide having a contact surface that is complementary to the anatomy of the patient in accordance with some embodiments.
Figure 9:
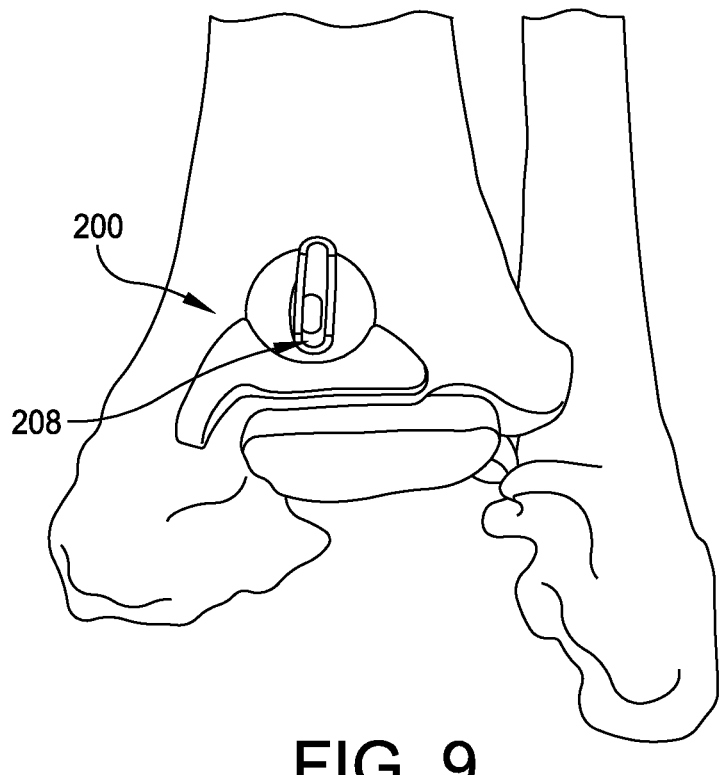
FIG. 9 is an anterior view of the burr guide of FIG. 8 in place on a patient in accordance with some embodiments.

A system or kit according to embodiments described herein can further include a burr guide to guide a burr, such as any of burrs 100, 110, 120, 130, during use. FIGS. 5 and 6 show one example of a burr guide 200 in accordance with some embodiments. The burr guide 200 includes a body 202 having a contact surface 204, a guide surface 206 spaced apart from the contact surface 204, and a guide channel 208 extending between the contact surface 204 and the guide surface 206 (best seen in FIG. 6). The contact surface 204 is configured to contact tissue of a patient during use. In some embodiments, (as shown in FIGS. 8 and 9) the burr guide 200 is patient specific. In such embodiments, the contact surface 204 can include a surface topology that is complementary to the anatomy of the patient. For example, the contact surface 204 can be configured to conform to a portion of the patient's ankle. It should be understood that the burr guide 200 need not be patient specific. For example, in various embodiments, the burr guide 200 has a contact surface 204 that is contoured to fit an average topology of patient anatomy. Alternatively or additionally, burr guides 200 can be provided in various sizes and configurations (e.g., small, medium, large) to allow a surgeon to choose the most appropriate guide at the time of operation.

In some embodiments, the contact surface 204 of burr guide 200 is patient specific. One example of such a patient-specific contact surface 204 is shown in FIGS. 8 and 9. Patient-specific surfaces may be created using conventional methods, such as disclosed in U.S. Pat. No. 5,768,134, entitled "Method for Making a Perfected Medical Model on the Basis of Digital Image Information of a Part of the Body," and U.S. Pat. No. 9,017,334, entitled "Patient Specific Surgical Guide Locator and Mount," the entireties of which are incorporated by reference herein.

Further, in some embodiments, the burr guide 200 includes spikes 210 or other projection extending from the contact surface 204 to secure the burr guide 200 to the patient during use. The spikes 210 can be integrally formed with the body 202 or, alternatively, can be separate components that are joined to the body 202 using fasteners, adhesive, or other means. Alternatively or additionally, the contact surface 204 can be textured or knurled to help secure the burr guide 200 to the patient. A portion of the burr guide 200 can also be configured to engage a portion of an implant to locate the burr guide 200.

The guide channel 208 is configured to receive a burr for removing bone. Although burr 110 is shown in FIG. 6, one of ordinary skill in the art will understand that other burrs, such as burrs 100, 120, 130, may be used with burr guide 200 and received within guide channel 208. The guide channel 208 is configured to allow the burr 110 to be swept along a path corresponding to a portion of bone to be removed. The guide channel 208 includes a first opening 212 at the contact surface 204 and a second opening 214 at the guide face 206. In some embodiments, the first opening 212 is smaller than the second opening 214. The second opening 214 may be in the form of an elongated slot such that the burr can be pivoted within the guide channel 208. In some embodiments, the guide channel 208 is configured to correspond to a surface of an implant to allow the burr to be swept along the surface of the implant, as described further herein.

In embodiments in which the burr includes a depth stop (e.g., depth stop 119), the guide surface 206 is configured to contact the depth stop 119 to control the depth of insertion of the burr 110. The guide surface 206 can be arcuate such that the depth of the tip of the burr remains constant as the burr is pivoted in the guide channel 208. In other words, the distance from the contact surface 204 to the guide surface 206 can vary as the guide surface 206 follows its arcuate path to control the depth of insertion of the burr. For example, the portion of the guide surface 206 that is nearer the center of the second opening 214 can be further from the contact surface 204 than is the portion of the guide surface 206 that is nearer the ends of the second opening 214, as shown best in FIG. 6.

Figure 7:
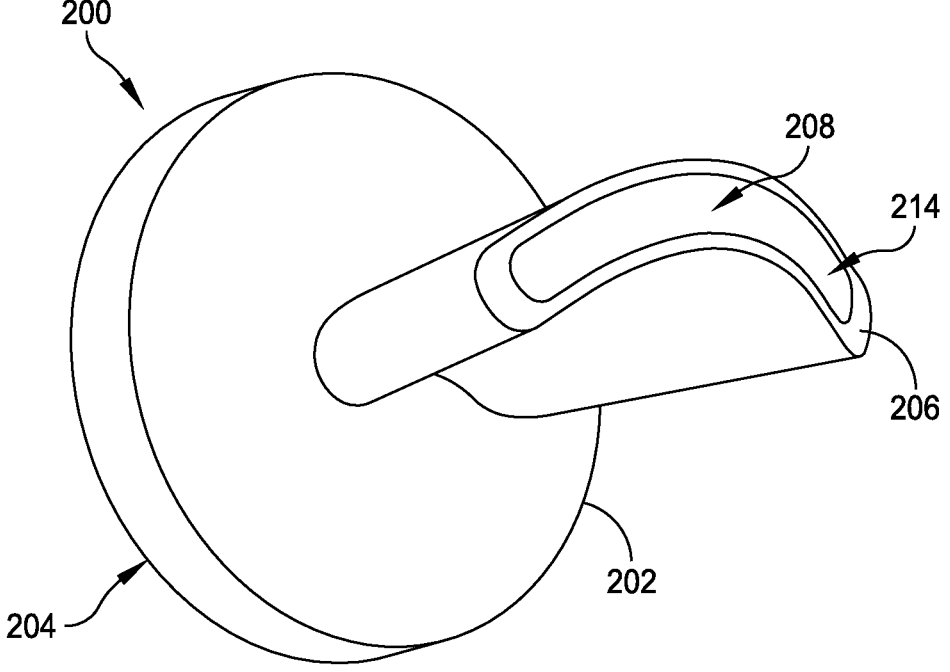
FIG. 7 is a front perspective view of a burr guide in accordance with some embodiments.

In some embodiments, the guide channel 208 is curved, as shown in FIG. 7. In other words, the guide channel 208 curves around an axis that extends from the contact surface 204 to the guide surface 206. This may allow the burr to be swept along a curved path to remove a curved portion of bone. For example, such a burr guide 200 can be used to remove bone around the top of a tibial stem. In such embodiments, when in place on the patient, the center of the second opening 214 is higher than (or superior to) the ends of the second opening 214.

Figure 10:
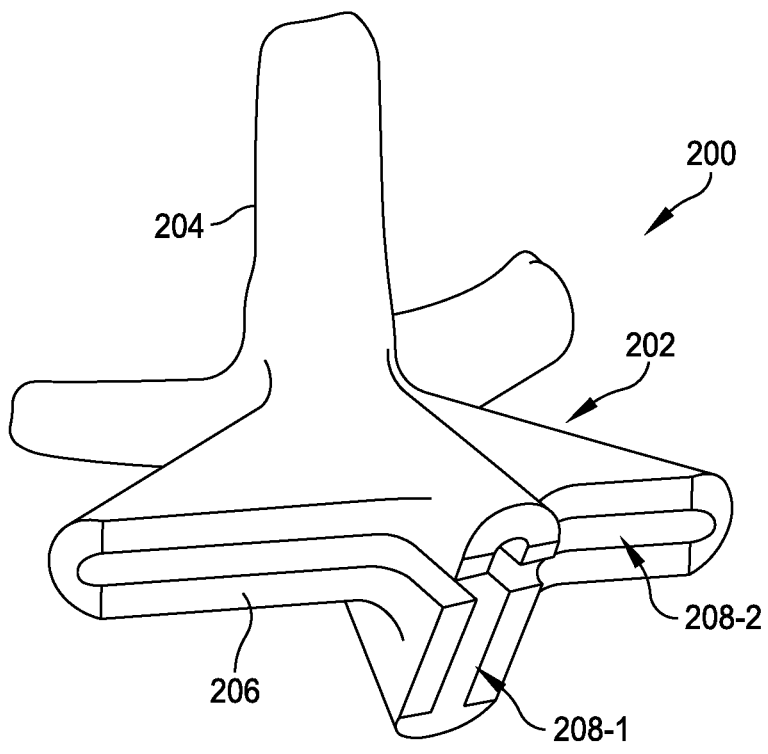
FIG. 10 is an isometric view of one example of a burr guide including multiple guide channels that intersect one another in accordance with some embodiments.
Figure 11:
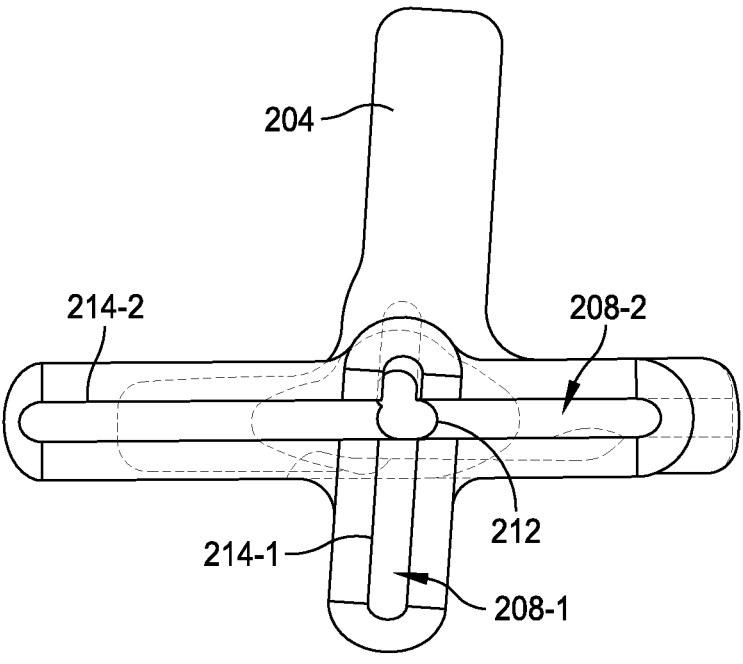
FIG. 11 is a front view of the burr guide illustrated in FIG. 10 in accordance with some embodiments.

In some embodiments, the burr guide 200 comprises multiple guide channels (which can be separate channels) or a single guide channel with multiple branches that intersect one another. One example of such an implant is shown in FIGS. 10-11. As best seen in FIGS. 10 and 11, burr guide 200 includes a first guide channel or branch 208-1 extending from opening 212 to opening 214-1 and a second guide channel or branch 208-2 extending from opening 212 to opening 214-2. The first guide channel 208-1 may be oriented in a first direction defining a first cutting plane and the second guide channel 208-2 may be oriented in a second direction defining a second cutting plane. In some embodiments, the first and second cutting planes are non-parallel cutting planes, which may allow a burr to remove bone from more than one aspect of an implant, as described further herein. In some embodiments, such as the embodiment shown in FIGS. 10-11, the first and second guide channels 208-1, 208-2 intersect such that a burr can be traversed through the guide channel without removing the burr from the burr guide.

In some embodiments, the burr guide 200 includes one or more radio-opaque members such that placement and alignment of the burr guide 200 is verifiable using fluoroscopy. For example, the radio-opaque members or features may be oriented in the same axis as the implant that is to be removed. The fluoroscopy checks may be implemented as a wired that is arranged such that it is aligned with the existing implant or stem when the burr guide is properly placed. Additionally or alternatively, a wire or other radio-opaque member may be supported by the burr guide such that when the burr guide is properly placed the wire or radio-opaque member matches the broad horizontal surface of the implant or an edge of the implant. In some embodiments, the burr guide may include one or more radio-opaque members that collectively provide an outline of the implant that is to be removed, such as is disclosed in U.S. Pat. No. 10,105,151, entitled "Instrument for Intra-Operative Implant Templating Using Fluoroscopy," and/or a "gun sight" as disclosed in U.S. Pat. No. 9,402,640, entitled "Alignment Guide with Embedded Features for Intra-Operative Fluoro-Checks," the entireties of which are incorporated by reference herein.

It should be understood that the rotating tool guides described herein may also be configured to engage fixtures or other alignment devices such that the guides do not directly contact a patient. For example, any number of extra- or intramedullary guides or fixtures are known to be used in performing joint replacement surgeries, and the contact surface of the tool guides may be adapted to contact and/or be coupled to such fixtures with directly contact the patient. The coupling between the guide and the fixture may also take a variety of forms, including couplings through mechanical (e.g., a clamp, clip, dovetail, mortise and tenon joint) or adhesive means. In some embodiments, the guides may be configured to engage a surface of an implant or component of an implant. For example, the contact surface of the guide may be configured to engage or otherwise be coupled to a "lock-detail" surface of an implant such that the guide may be coupled and locked to an implant while used. Examples of implant surfaces to which a guide may be coupled include, but are not limited to, surfaces where the poly-insert mates to the tibia implant, and/or the anterior surface of the implant which is frequently easy to access. In such embodiments, the guide may have channels to guide the burr along the implant's bone-contacting features such as any tibia stem feature, and proximal, medial and lateral surfaces of the tibia implant as described below. The guide may also be implemented with one or more outriggers to allow for approaching the implant from any direction, especially from medial, lateral, anterior or posterior directions. Thus, the contact surfaces of the guides may be configured to facilitate the locating of the guide relative to a patient.

Figure 12:
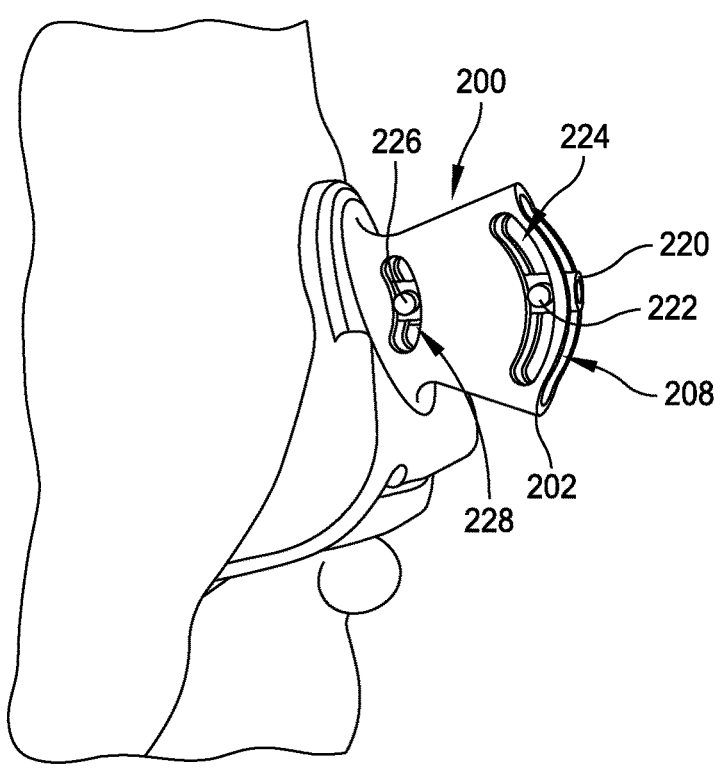
FIG. 12 is a perspective view of one example of a burr guide that includes a sleeve in place on a patient in accordance with some embodiments.
Figure 13:
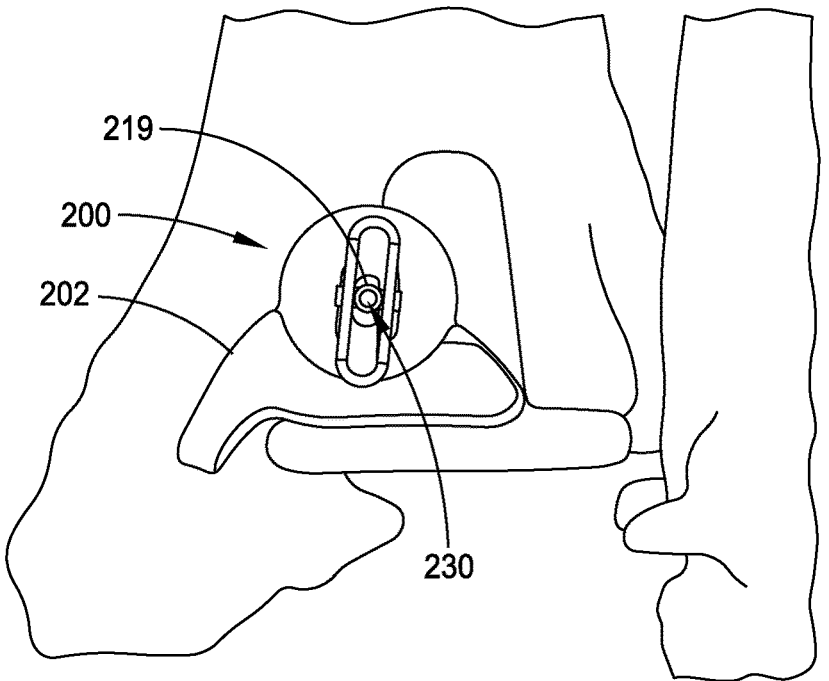
FIG. 13 is an anterior view of the burr guide of FIG. 12 in place on a patient in accordance with some embodiments.

In some embodiments, such as the embodiments shown in FIGS. 12 and 13, the burr guide 200 includes a sleeve 220 configured to receive a burr (e.g., burr 100, 110, 120, 130). The sleeve 220 is configured to be positioned and translate within the guide channel 208. The burr guide 200 can include a first pin 222 extending from the sleeve 220. In such embodiments, the body 202 defines a slot 224 that extends through the body 202 such that the slot 224 communicates with the guide channel 208. The pin 222 may be positioned within the slot 224 to guide movement of the sleeve 220 within the guide channel 208. The burr guide 200 also may include a second pin 226 extending from the sleeve 220, and the body 202 may define a second slot 228 extending through the body 202 such that the slot 228 communicates with the guide channel 208. The second pin 206 may be positioned within the second slot 228 to guide movement of the sleeve 220 within the guide channel 208. The first and second pins 222, 226 guide the movement of the sleeve 220 in a pivoting motion in the guide channel 208. For example, the slots 224, 228 can each follow an arcuate path to guide the sleeve 220 as desired. In some embodiments, the slots 224, 228 are spaced apart along an axis that extends away from the contact surface 204 and follow arcuate paths that are concentric with one another. The slots 224, 228 can also be concentric with the guide surface 206. The slots 224, 228 can extend through one or both walls of the burr guide 200 defining the guide channel 208. In embodiments in which the slots 224, 228 extend through both walls, the pins 222, 226 can be positioned such that they are positioned in the slots 224, 228 defined in both walls.

As best seen in FIG. 13, the sleeve 220 includes a bore 230 for receiving a burr (e.g., burr 100, 110, 120, 130). The sleeve 220 can be constructed of a relatively hard material to ensure that rotation of the burr within the bore 230 does not remove material from the sleeve 220 to prevent such material from being introduced to the patient's body.

Figure 17:
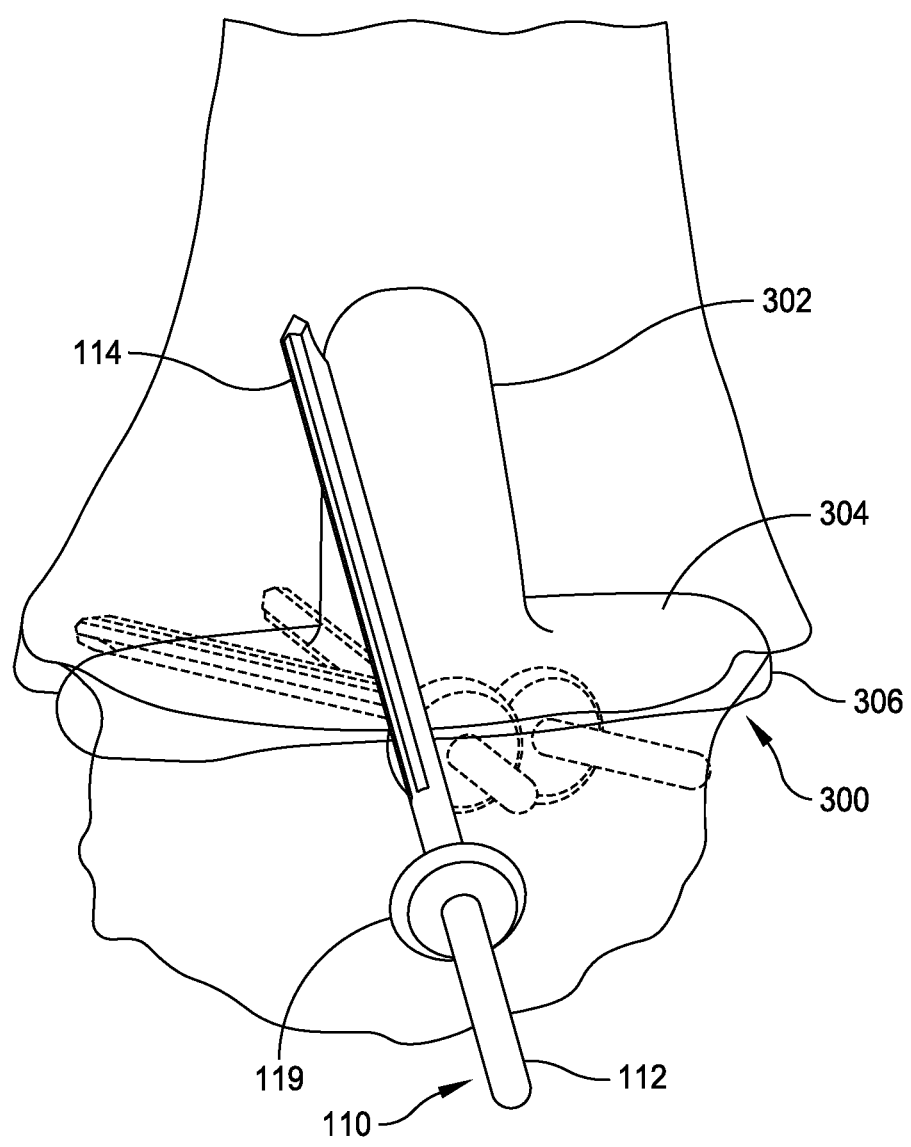
FIG. 17 is a perspective view of a burr in use to remove bone adjacent to a stem and a platform of an implant in accordance with some embodiments.
Figure 18:
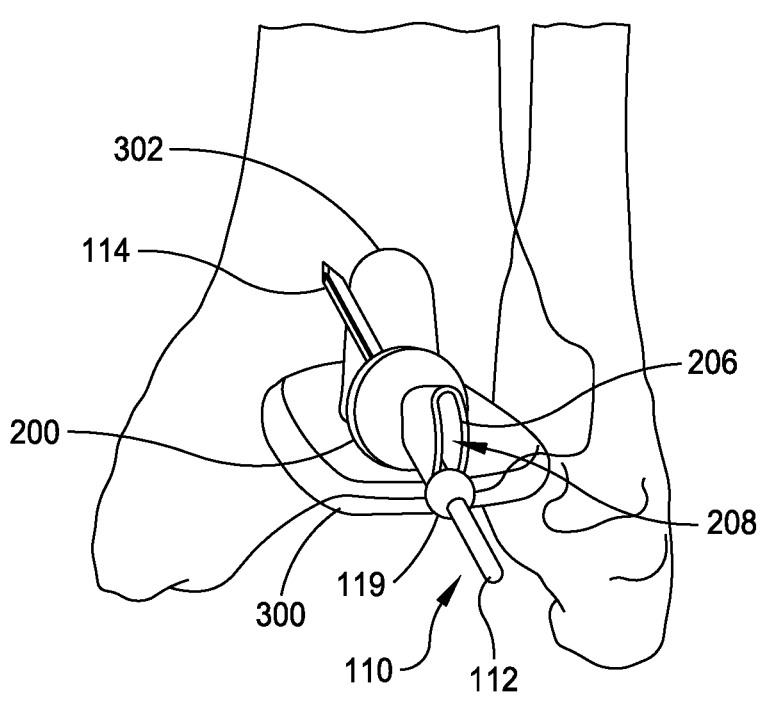
FIG. 18 is a view from the anterior-medial direction (e.g., a front view) of a burr and burr guide in use to remove bone adjacent to a stem of an implant in accordance with some embodiments.
Figure 19:
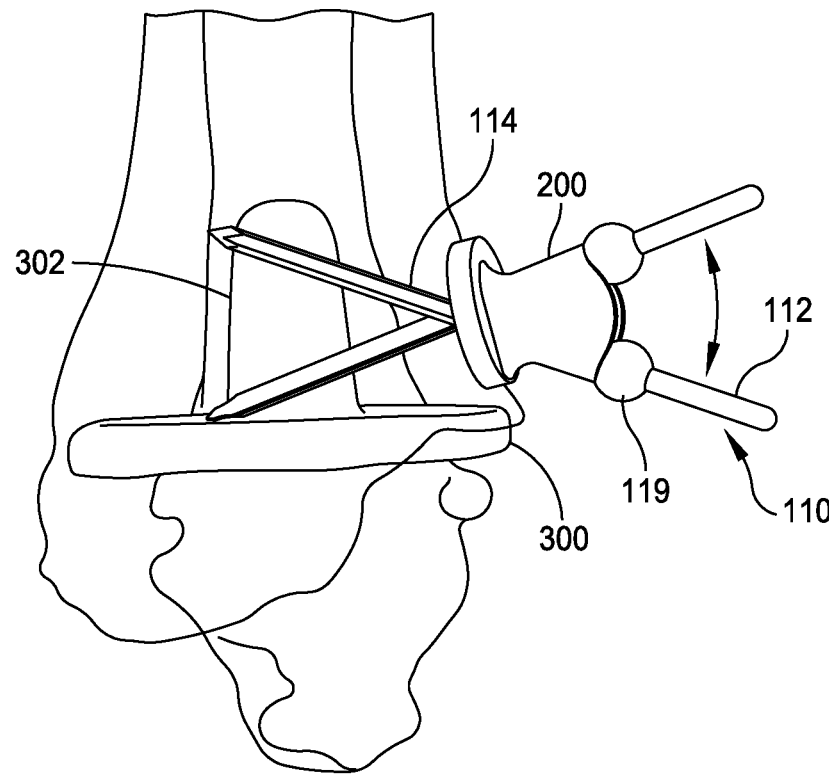
FIG. 19 is a medial view of a burr and a burr guide in use to remove bone adjacent to a stem of an implant in accordance with some embodiments.
Figure 20:
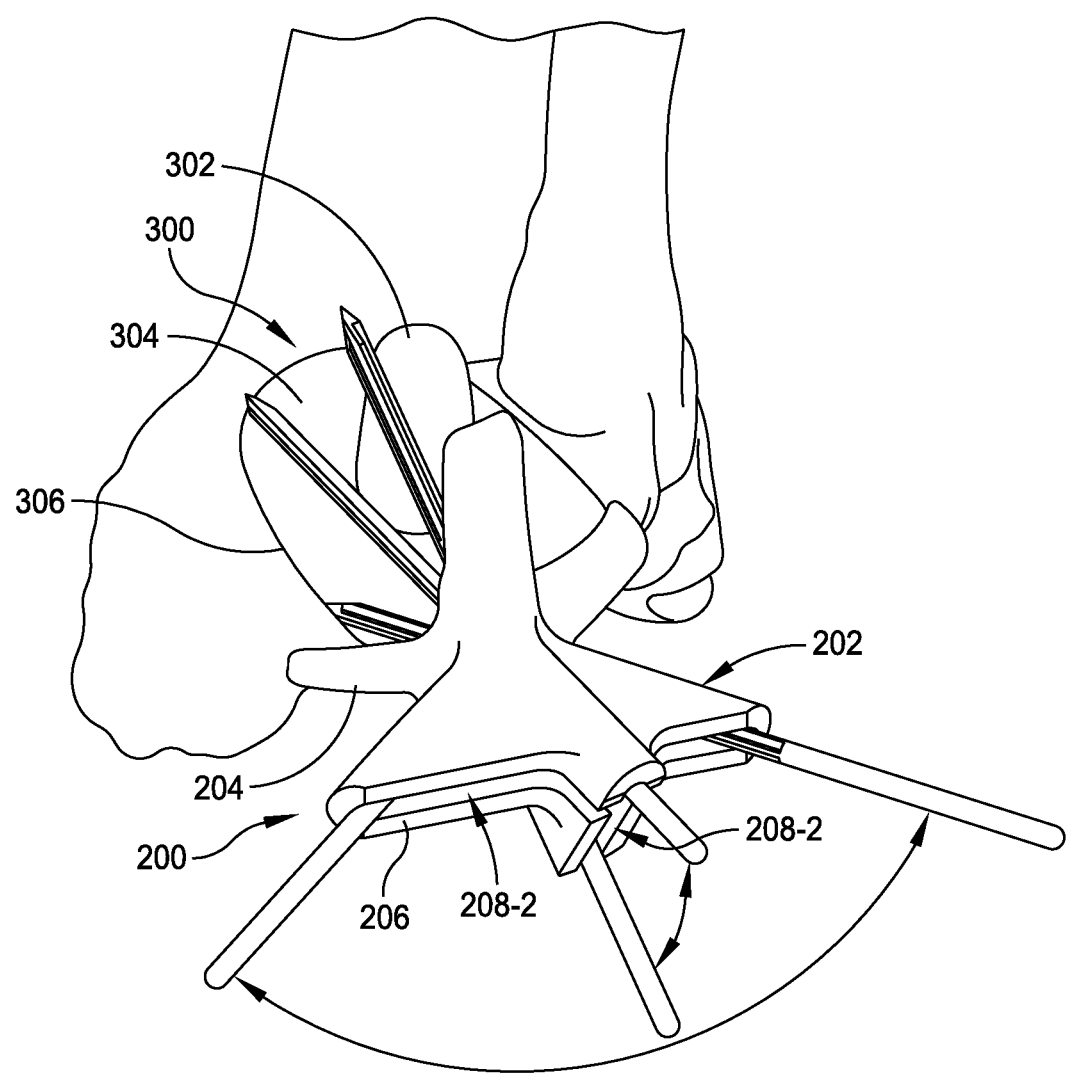
FIG. 20 is an anterior perspective view of a burr and a burr guide in use to remove bone adjacent to a step of an implant in accordance with some embodiments.
Figure 21:
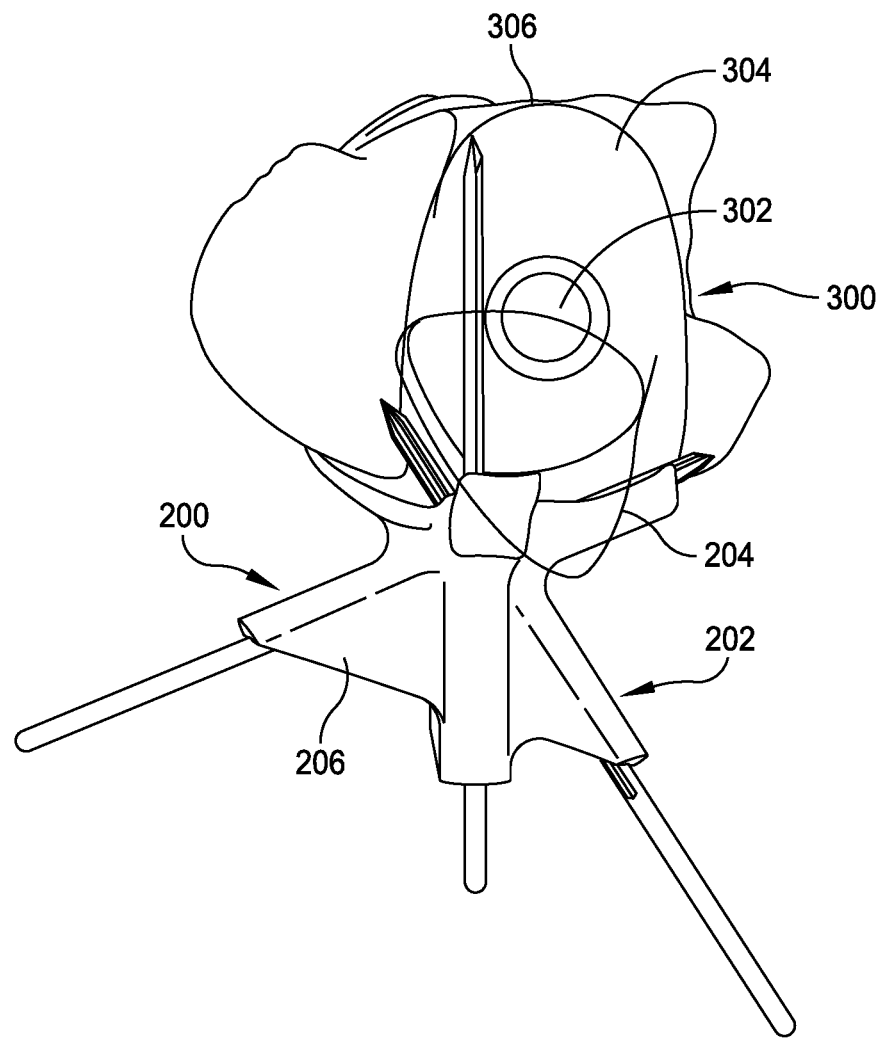
FIG. 21 is a superior view of the burr and burr guide illustrated in FIG. 20 in use in accordance with some embodiments.
Figure 22:
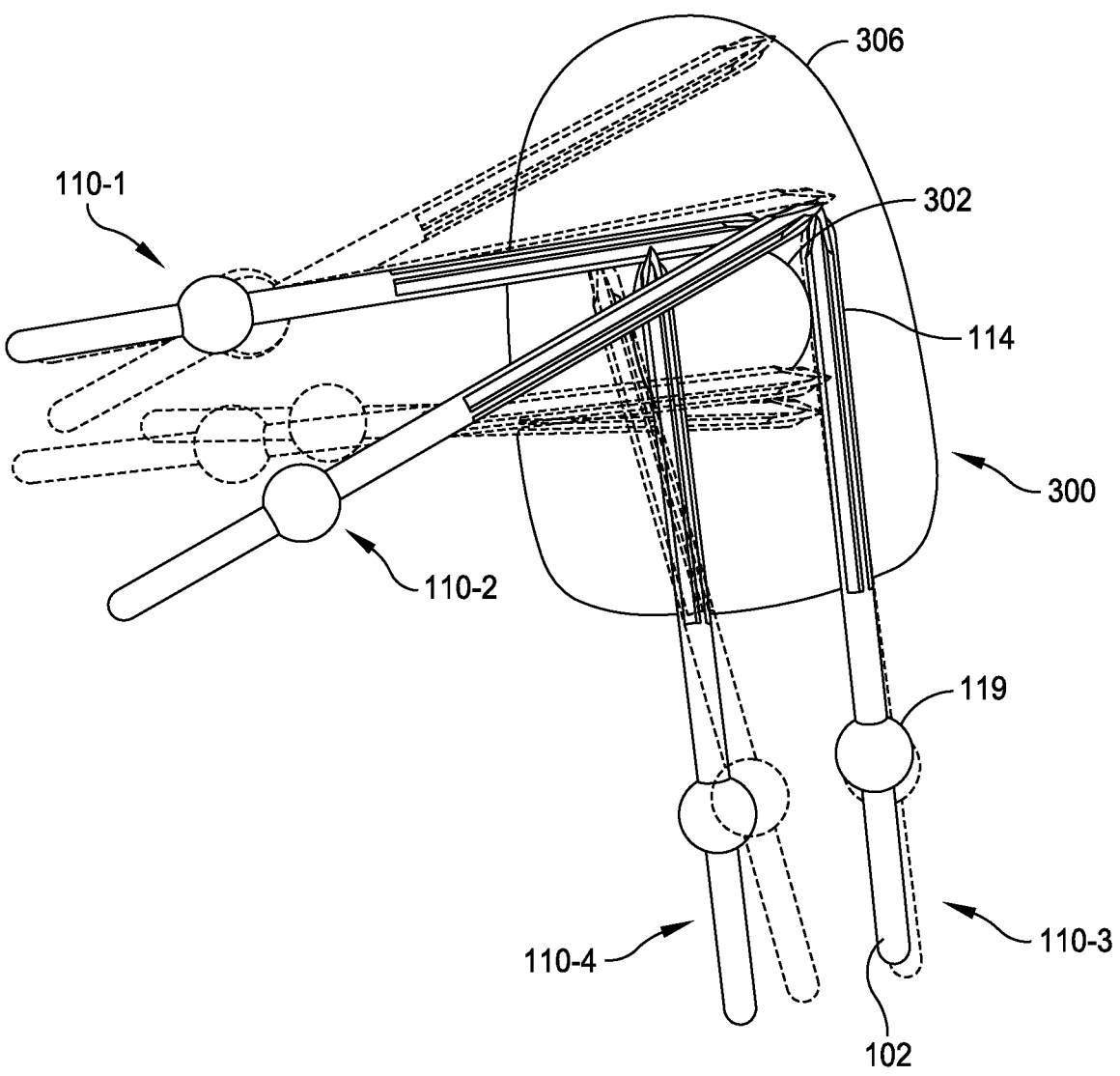
FIG. 22 is a superior view illustrating one example of various paths and incision points for a burr removing an implant in accordance with some embodiments.

FIGS. 14-22 illustrate methods of removing an implant 300 using a burr. More particularly, FIGS. 14-17 illustrate the use of the burr 110 without the assistance of a burr guide 200; FIGS. 18-19 illustrate a method of using a burr with the assistance of a burr guide having a single channel; FIGS. 20-21 illustrate a method of using a burr with the assistance of a burr guide having multiple channels that intersect one another; and FIG. 22 illustrates a method of using a burr with multiple access incisions. Although burr 110 is depicted in FIGS. 14-22, it should be understood that other burrs described herein (e.g., burrs 100, 120, 130) can be used in a similar manner.

Figure 14:
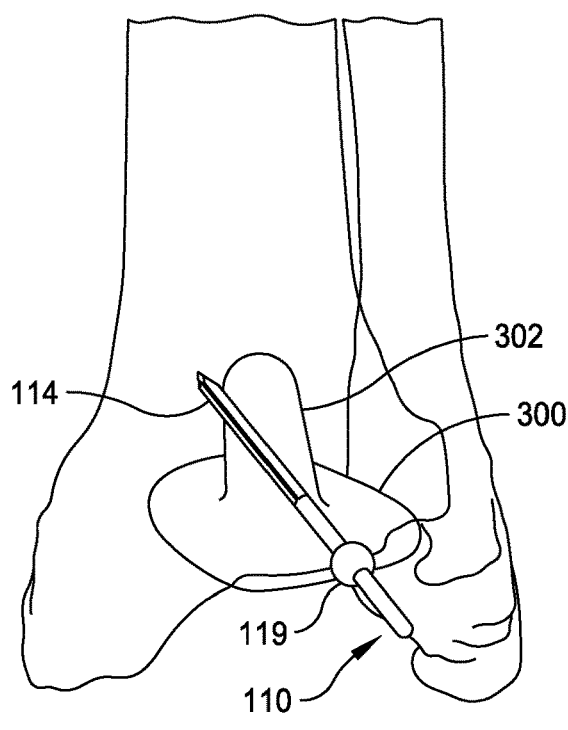
FIG. 14 is a view from the anterior-medial direction (e.g., a front view) of a burr in use to remove bone adjacent to a stem of an implant in accordance with some embodiments.
Figure 15:
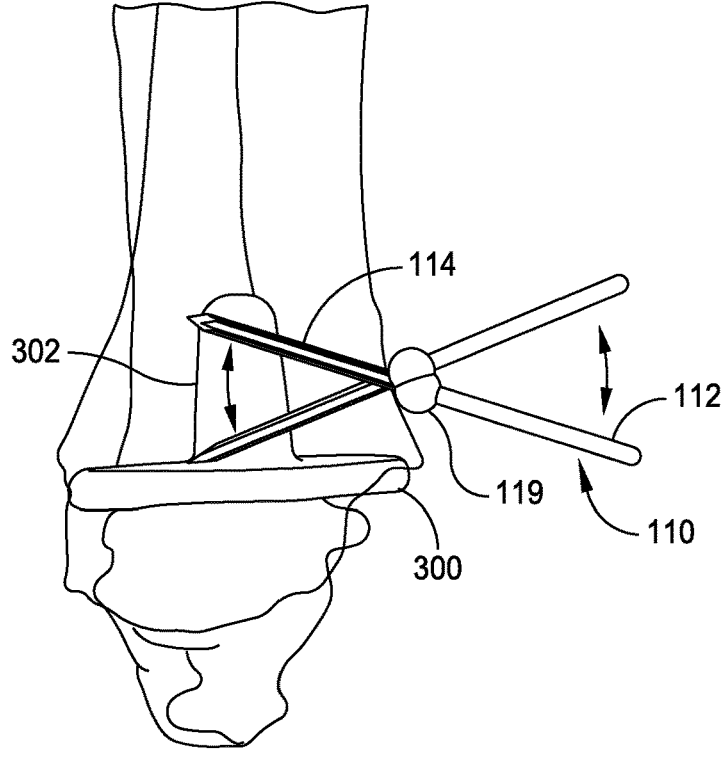
FIG. 15 is a medial view of a burr in use to remove bone adjacent to a stem of an implant in accordance with some embodiments.
Figure 16:
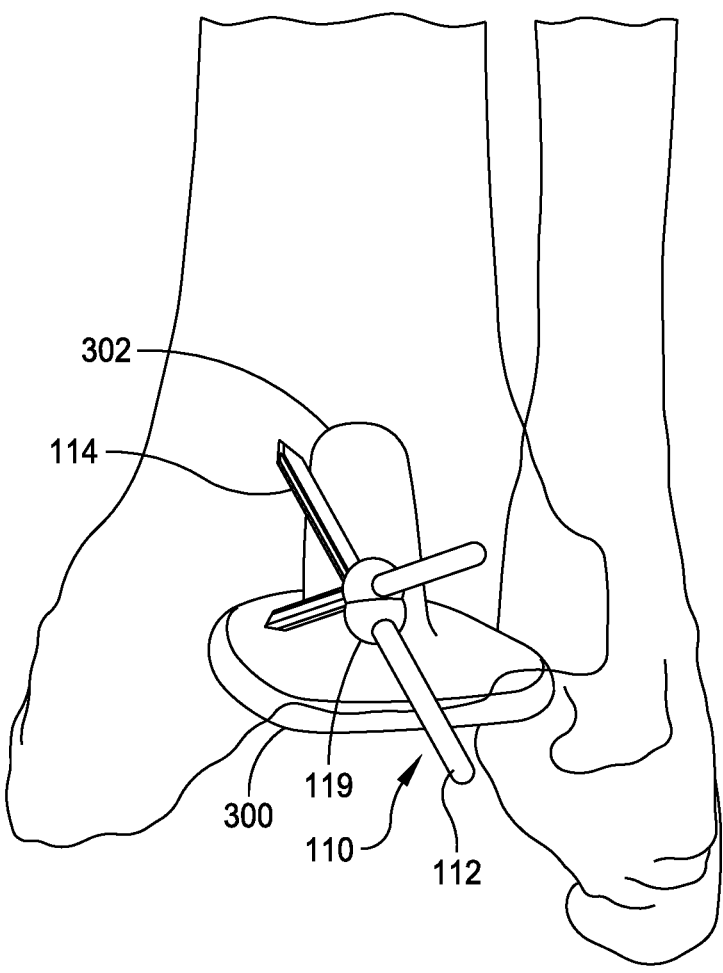
FIG. 16 is a view from the anterior-medial direction (e.g., a front view) of a burr in use to remove adjacent a stem of an implant in accordance with some embodiments.

Referring first to FIGS. 14-17, an incision is formed in tissue of a patient as the desired point of entry. Various incision points (e.g., anterior, posterior, medial, lateral) can be used, as described in more detail herein and as will be understood by one of ordinary skill in the art. The burr 110 is then inserted in the incision as shown in FIG. 14. The burr 110 is then pivoted such that the tip of the burr 110 is swept upward and downward, as shown by the arrows in FIG. 15, while the burr 110 is rotated about its longitudinal axis. As a result, the burr 110 removes bone and/or bone cement adjacent to the implant stem 302. The depth stop 119 contacts the anterior surface of the bone, or possibly the skin of the patient and the burr 110 can be pivoted about the depth stop 119. In some embodiments, the depth of insertion and movement of the burr 110 can be controlled by a robotic arm or other robotic assisted surgery technology. The burr 110 can follow pre-programmed paths or the paths of the burr can be determined by the surgeon during surgery. Additionally or alternatively, the depth of insertion and movement of the burr 110 can be viewed and verified using fluoroscopy or other imaging modality.

As shown in FIG. 17, the burr 110 can be swept along two paths while inserted through the first incision. For example, the burr 110 can be swept along a side of the stem 302 of the implant 300 as well as along the top surface 304 of the implant base plate 306. This may allow the implant to be removed while minimizing the number of incisions made in the patient's tissue.

FIGS. 18 and 19 show use of the burr 110 with one example of a burr guide having a single guide channel. In such embodiments, the burr guide 200 is placed against the patient, either before or after the forming of the incision in the tissue of the patient as described above. The burr 110 is inserted through the guide channel 208 until the depth stop 119 comes into contact with the guide surface 206. The burr 110 is then pivoted in the guide channel 208, as indicated by the arrow shown in FIG. 19, to sweep the cutting portion 116 of the elongated shaft 102 along a surface of the implant (e.g., along the stem 302 of the implant 300).

FIGS. 20 and 21 show the use of a burr 110 with the burr guide 200 illustrated in FIGS. 10 and 11 (i.e., a burr guide with two channels 208-1, 208-2 that intersect one another). As best seen in FIG. 20, the burr 110 can be swept along two paths while inserted through a single incision. For example, the burr 110 can be swept along a side of the stem 302 of the implant 300 being guided by channel 208-2 as well as be swept along the top surface 304 of the implant base plate 306 being guided by channel 208-1. This may allow the implant to be removed while minimizing the number of incisions made in the patient's tissue.

By removing bone along two surfaces of the implant through one incision, the number of incisions can be minimized, thereby minimizing the pain and discomfort for the patient. It also minimizes the total amount of bone removed compared to conventional methods, which include cutting out a chunk of bone that matches the shape of the entire profile of the tibia implant and stem. That bone is removed in order to access the stem. In contrast, the guides and methods disclosed herein advantageously releases the implant (e.g., a tibial stem) from the adjacent bone or cement while preserving the front of the bone (e.g., the (anterior) cortex). Once the implant is freed the implant can be extracted distally, rather than pulled through the anterior cortex.

As illustrated by FIG. 22, the method can include forming and inserting a burr (e.g., burr 100, 110, 120, 130) through multiple incisions in the patient's tissue. For example, the method can include forming two substantially medial-lateral incisions and two substantially posterior-anterior incisions. This may allow the user to use a burr to remove bone from each side of the stem 302 of the implant 300. Although burr 110 is shown in FIG. 22, one of ordinary skill in the art will understand that other burrs, e.g., burrs 100, 120, 130, may be used in a similar manner.

The burr identified with reference numeral 110-1 in FIG. 22 represents a burr being inserted in a first incision and being swept along two different paths. For example, a first pass of the burr may be along a side of the stem 302 (e.g., the anterior side), and a second path along the top 304 of the implant platform 306. The burr identified with reference numeral 110-2 in FIG. 22 represents a burr, which can be the same burr as burr 110-1 or a different burr, being inserted in a second incision and being swept along a second side of the stem 302 (e.g., posterior side) as well as over the top of the stem 302. It should be understood that the burr can be guided by a burr guide with a guide channel that is at least partially curved to allow the guide to pass over the curved top of the stem 302. Burrs 110-3 and 110-4 in FIG. 22 represent a burr, which can be the same burr or a different burr from burrs 110-1 and 110-2, being inserted through the posterior-anterior incisions and run along the medial and lateral sides of the stem to remove bone therefrom. These burrs can also be swept along the top of the implant platform and/or over the top of the stem.

Removing the bone and/or bone cement adjacent to the stem 302 of the implant 300 and along the top 304 of the platform 306 may allow the implant 300 to be removed from the bone. Using a burr to remove material from the implant 300 and removing the implant 300 in this way may allow for removal of the implant with less trauma to the patient than using more invasive prior art techniques. This may allow for a faster or easier recovery for the patient and less post-procedure pain.

In another aspect, the burrs and burr guides described herein can be used to prepare a bone for implantation of a new implant, not just to remove a previously implanted implant. The burr can be swept along paths to form a cavity in the bone for receiving an implant (e.g., a stem), similar to the methods described above. The paths can be selected based on the geometry of the implant and its desired position in the bone. As with the methods described above, the burrs can be swept using robotic-assisted techniques and can be based on surgical planning.

Figures 23, 24, 25:
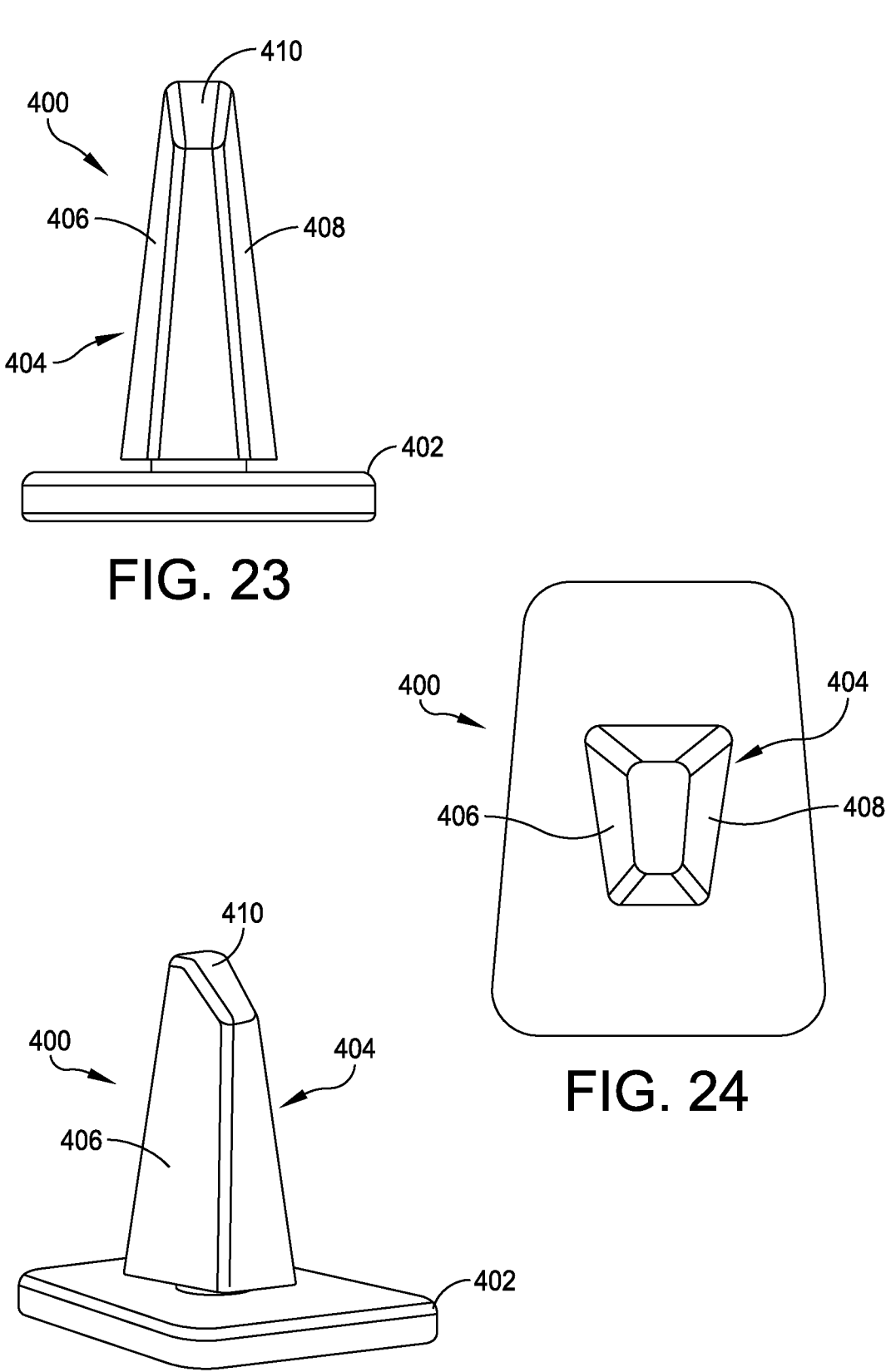
FIG. 23 is an anterior view of one example of an implant in accordance with some embodiments.
FIG. 24 is a superior view of the implant of FIG. 23 in accordance with some embodiments.
FIG. 25 is a perspective view of the implant of FIG. 23 in accordance with some embodiments.

In another aspect, an implant specifically configured for implantation in a bone cavity prepared with burrs in the manner described above are provided. FIGS. 23-25 show one embodiment of such an implant 400. The implant 400 includes a platform 402 and a stem 404. The stem 404 is configured to be inserted into a cavity in a bone prepared by sweeping burrs along a desired path, as described herein. The stem 404 has a first face 406 (e.g., a lateral face), a spaced apart second face 408 (e.g., a medial face), an third face 410 (e.g., an anterior face) that extends between the first face 406 and the second face 408, and a fourth face 412 (e.g., a posterior face) that extends between the first face 406 and the second face 408 and is spaced apart from the third face 410.

Fillets may be formed at the intersections of the faces. In some embodiments, each of the faces 406, 408, 410, and 412 define a substantially planar surface. The lateral 406 and medial 408 faces are inclined relative to one another about at least one axis. The first 406 and second 408 faces may be inclined with respect to one another about two axes.

For example, as shown in FIG. 23, the first face 406 and the second face 408 are inclined relative to one another about the y-axis (as shown in FIGS. 23 and 24). When the implant 400 is implanted, the y-axis may be substantially aligned in the superior-inferior orientation. Further, the first face 406 and the second face 408 also may be inclined relative to one another relative to the z-axis. When the implant 400 is implanted, the z-axis may be substantially aligned in the anterior-posterior orientation.

The inclination relative to the z-axis causes the stem 404 to be wider at the bottom (i.e., near the platform) than at the top of the stem 404. The inclination relative to the y-axis causes the stem 404 to be wider at a first (e.g., posterior) side than at a second (e.g., anterior) side. As described in more detail hereinafter, the inclination of the faces of the implant allow the cavity of the bone into which the implant will be inserted to be prepared with fewer perforations of the cortical bone than would be required for an implant having a traditional stem. The third and fourth faces 410, 412 may be inclined relative to one another relative to the x-axis. When the implant 400 is implanted, the x-axis may aligned in a substantially medial-lateral orientation.

Figure 26:
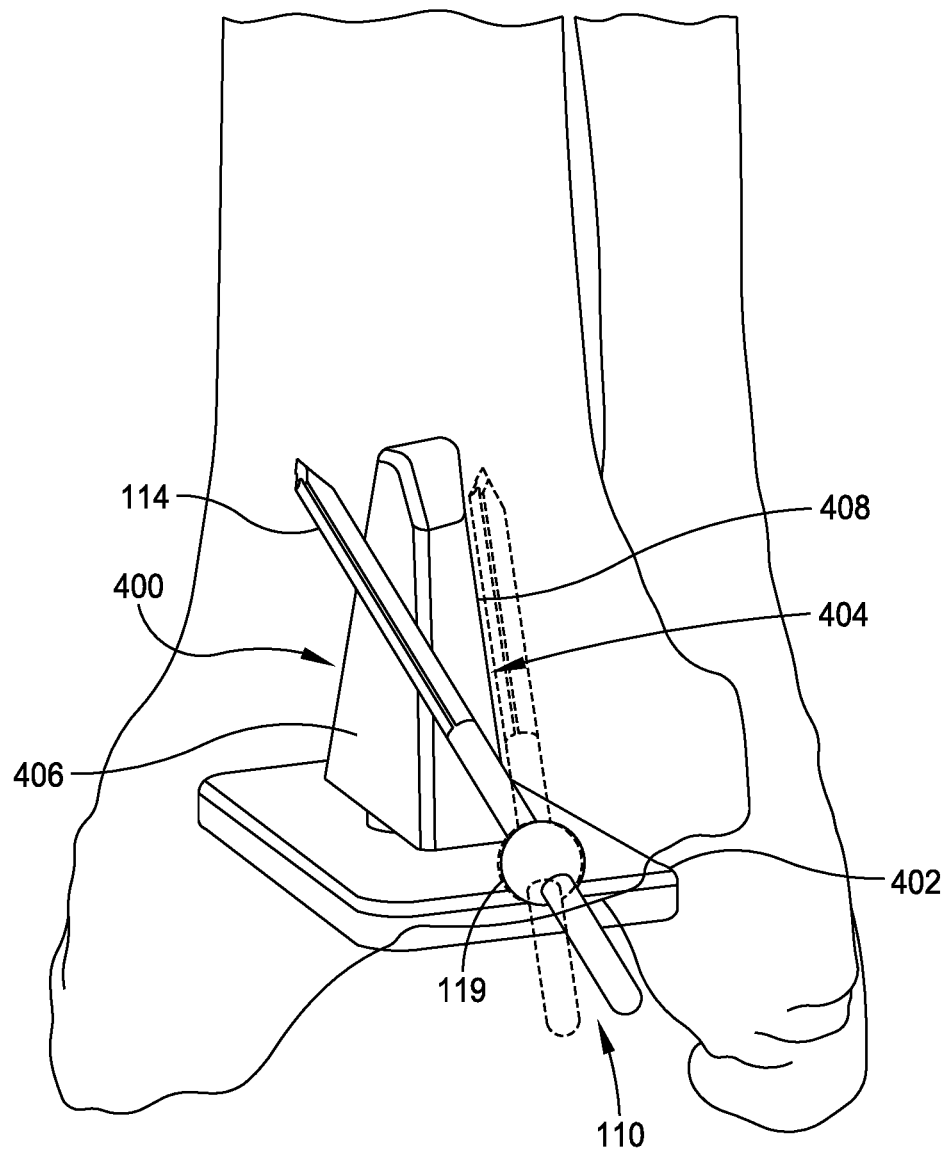
FIG. 26 is a perspective view of a burr in use to prepare a cavity in a bone for implantation of the implant of FIG. 23 in accordance with some embodiments.

The cavity in the bone can be formed according to the methods described above. Because of the arrangement of the faces of the stem 404, the stem 404 can fit in a cavity formed in a bone using a limited number of incisions. FIG. 26 illustrates the forming of the cavity for the stem 404. The implant 400 is shown in this figures for the purposes of illustration; however, it should be understood that the implant 400 would not be in place during formation of the cavity.

As shown in FIG. 26, an incision can be formed in an aspect (e.g., an anterior aspect) of the patient's anatomy. Through this incision, the medial and lateral aspects of the bone cavity can be formed by sweeping the burr along what will be the portion of the cavity that will be in contact with, or adjacent to, the first face 406 and the second face 408. It is possible to form both sides of the cavity through a single incision because the first face 406 and the second face 408 are angled toward one another, as described above. In other words, the anterior portions of the first and second faces 406, 408 are closer to each other than they are closer to the posterior portions. It should be understood that in other embodiments, the posterior portions of the first and second faces 406, 408 are closer to one another than are the anterior portions of the first and second faces 406, 408. With such a configuration, the medial and lateral aspects of the cavity can be prepared using a posterior incision.

In some embodiments, the medial and lateral aspects of the cavity are formed through separate incisions. This may reduce the amount of bone removed through each incision and balance the removal of the bone. As a result, recovery for the patient may be less painful and more rapid.

The anterior and posterior aspects of the cavity can be prepared through medial and/or lateral incisions. In some procedures, both the anterior and posterior aspects of the cavity can be prepared through incisions on the same side (e.g., either the medial or lateral side). In other procedures, the anterior and posterior aspects of the cavity are formed through incisions on opposite sides of the bone, with one being prepared through a medial incision and one being prepared through a lateral incision. Placing the incisions on opposite sides of the bone may balance the bone loss and ease recovery from the procedure.

In some embodiments, at least a portion of the top 410 of the stem 404 is angled (e.g., from anterior to posterior) so that the top portion of the cavity can be prepared with a burr inserted through the same incision used to prepare either the anterior or posterior sides of the cavity (e.g., through a medial or lateral incision).

Figure 27:
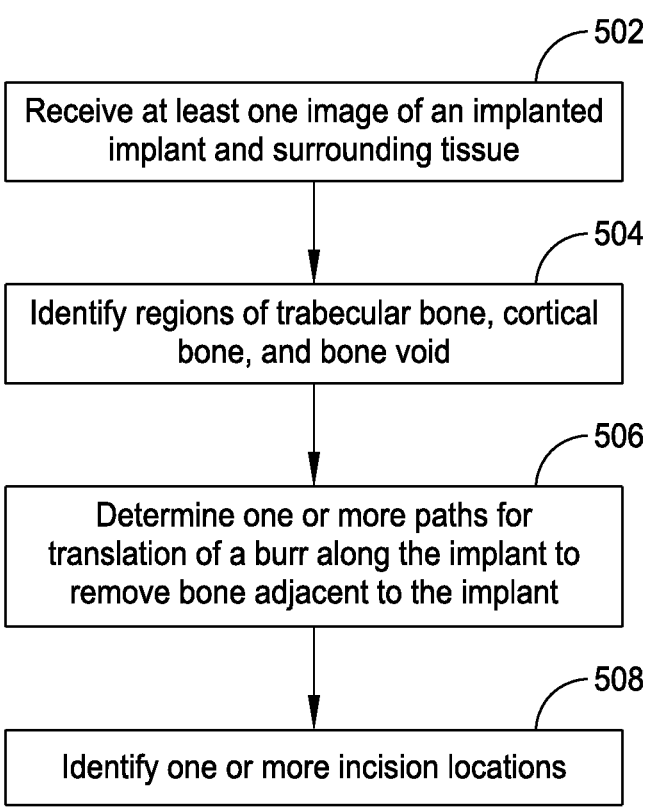
FIG. 27 is a flowchart illustrating a method of planning removal of an implant from a patient in accordance with some embodiments.

In another aspect, shown in FIG. 27, a method of planning removal of an implant is provided. The method includes, at step 502, receiving at least one image of the implant in the patient. The images can be developed using any of a variety of imaging modalities-including, for example, x-ray, computed tomography (CT), magnetic resonance imaging (MRI), or any other appropriate imaging modality. The method further includes, at step 504, identifying regions of trabecular bone, cortical bone, and bone void. The method further includes at step 506, determining one or more paths for translation of a burr along the implant to remove bone adjacent to the implant. The paths are configured to remove sufficient bone to allow removal of the implant while minimizing removal of cortical bone. In some embodiments, the paths are chosen to preferentially choose paths that pass through bone voids. The method may further include, at step 508, identifying one or more incision locations that allow entry of a burr into the patient's anatomy without damaging neurovascular bundles, ligaments, or tendons. The method can be performed manually—for example, by a surgeon—or in an automated fashion In some embodiments, a rotatable cutting tool for removing bone includes an elongated shaft and a depth stop. The elongated shaft has at least one cutting edge. The depth stop is coupled to the elongated shaft and outwardly extends from the elongated shaft. The depth stop is configured to contact tissue of a patient or a burr guide to restrict a depth of insertion of the elongated shaft.

In some embodiments, the depth stop is in the form of a sphere. In some embodiments, the depth stop is in the form of a truncated cone. In some embodiments, the depth stop is adjustable along a length of the elongated shaft.

In some embodiments, the elongated shaft includes a plurality of stops. The depth stop is configured to engage one of the stops to locate the depth stop along the elongate shaft.

In some embodiments, the depth stop comprises a collar that is adjustable along the length of the elongated shaft. In some embodiments, the depth stop includes a set screw that is engaged with the collar such that rotation of the set screw secures the collar in position along the elongated shaft.

In some embodiments, the elongate shaft includes a cutting portion along which the at least one cutting edge extends and a non-cutting portion that does not contain a cutting edge. The depth stop is positioned along the non-cutting portion. In some embodiments, the depth stop is located along the non-cutting portion such that a first segment of the non-cutting portion is located between the depth stop and the cutting portion and a second segment of the non-cutting portion is located between the depth stop and an end of the tool.

In some embodiments, a guide for a rotating cutting tool includes a body having a contact surface a first guide channel. The contact surface is configured to facilitate locating the guide relative to a patient. The first guide channel is configured to receive a rotating tool for removing bone from the patient and to guide the rotating tool as the rotating tool is swept along a path.

In some embodiments, the first guide channel includes a first opening extending through the contact surface and a second opening extending through a guide face that is spaced apart from the contact surface. In some embodiments, the first opening is smaller than the second opening.

In some embodiments, the second opening is an elongated opening such that the rotating tool can be pivoted when disposed within in the first guide channel.

In some embodiments, the guide face is configured to engage a depth stop of the rotating tool to control a depth of insertion of the rotating tool. In some embodiments, the guide face is curved such that the depth of a tip of the rotating tool remains constant as the rotating tool is pivoted in the first guide channel.

In some embodiments, the contact surface is complementary to an anatomy of the patient.

In some embodiments, the body includes a second guide channel. The first guide channel defines a first mid-plane, and the second guide channel defines a second mid-plane. In some embodiments, the first and second mid-planes are non-parallel.

In some embodiments, the first guide channel is curved such that sweeping the rotating tool within the first guide channel sweeps the rotating tool along a curved path.

In some embodiments, spikes extend from the contact surface for securing the guide to the patient.

In some embodiments, the body supports at least one radio-opaque member for verifying a position of the guide using fluoroscopy.

In some embodiments, the first guide channel defines a path that corresponds to a profile of an implant. In some embodiments, the surface of the implant is a surface of a stem of a tibial implant. In some embodiments, the guide is configured to contact a portion of the implant to orient the guide.

In some embodiments, a sleeve is coupled to the body. The sleeve is configured to receive the rotating tool and to translate within the first guide channel. In some embodiments, at least one pin extends from the sleeve, and the body includes at least one slot extending through the body and into the first guide channel. The at least one slot is configured to receive the pin to guide movement of the sleeve within the first guide channel.

In some embodiments, a system and/or a kit includes a rotating cutting tool and a guide. The rotating cutting tool includes an elongated shaft having at least one cutting edge for removing bone from a patient. The guide has a body including a contact surface and a first guide channel. The contact surface is configured to position the guide relative to a patient. The first guide channel is configured to receive at least a portion of the elongated shaft of the rotating tool such that the rotating tool is guided as the at least one cutting edge is swept along a path.

In some embodiments, the first guide channel includes a first opening extending through the contact surface and a second opening extending through a guide face of the body that is spaced apart from the contact surface, and wherein the first opening is smaller than the second opening.

In some embodiments, the rotating tool further comprises a depth stop disposed along a length of the elongated shaft. In some embodiments, the guide face is configured to engage the depth stop of the rotating tool to control a depth of insertion of the at least one cutting edge.

In some embodiments, the guide face is curved such that the depth of insertion of a tip of the rotating tool remains constant as the rotating tool is swept in the first guide channel.

In some embodiments, the contact surface of the guide is contoured to be complementary to an anatomy of the patient.

In some embodiments, the body of the guide includes a second guide channel. The first guide channel defines a first mid-plane, and the second guide channel defines a second mid-plane. In some embodiments, the first and second mid-planes are non-parallel with each other.

In some embodiments, the guide channel is curved such that sweeping the rotating tool within the guide channel sweeps the rotating tool along a curved path.

In some embodiments, spikes extend from the contact surface of the guide for securing the guide to the patient.

In some embodiments, a fixation element adapted to secure the guide to the patient. In some embodiments, the fixation element is selected from the group consisting of k-wires and screws.

In some embodiments, the body of the guide supports at least one radio-opaque member for verifying a position of the guide using fluoroscopy.

In some embodiments, the guide channel defines a path that corresponds to a profile of an implant. In some embodiments, the surface of the implant is a surface of a stem of a tibial implant. In some embodiments, the guide is configured to contact a portion of the implant to orient the guide.

In some embodiments, the guide further comprises a sleeve coupled to the body, and the sleeve configured to receive the rotating tool and to translate within the guide channel.

In some embodiments, the guide further includes at least one pin extending from the sleeve. The body defines at least one slot extending through the body and into the guide channel, and the at least one slot is configured to receive the pin to guide movement of the sleeve within the guide channel.

In some embodiments, the contact surface is configured to engage a surface of an implant.

In some embodiments, a method includes forming a first incision in tissue of a patient; inserting an elongated shaft of a rotating tool into the first incision such that a cutting edge disposed along a length of the elongated shaft is adjacent to a first surface of the implant; and sweeping the cutting edge along a first path adjacent to the surface of the implant to remove bone or bone cement adjacent to the first surface of the implant.

In some embodiments, the method includes forming a second incision in tissue of the patient; inserting the elongate shaft of the rotating tool into the second incision such that the cutting edge disposed along the length of the elongated shaft is adjacent a second surface of the implant; and sweeping the cutting edge along a second surface of the implant to remove bone adjacent to the second surface of the implant.

In some embodiments, a direction of approach of the first incision and a direction of approach of the second incision are different.

In some embodiments, the direction of approach of the first incision is parallel to the direction of approach of the second incision. In some embodiments, the first incision is in a generally medial to lateral direction and the second incision is in a generally posterior to anterior direction.

In some embodiments, the method includes placing a guide relative to the patient; and inserting the elongated shaft of the rotating tool through a guide channel of the guide. In some embodiments, the guide channel includes a first opening extending through a contact surface and a second opening extending through a guide face that is spaced apart from the contact surface. In some embodiments, the first opening is smaller than the second opening.

In some embodiments, the method includes inserting the elongated shaft of the rotating tool into a sleeve disposed in the guide channel of the guide.

In some embodiments, the rotating tool is controlled by a robotic arm.

In some embodiments, an implant includes a stem configured to be inserted into a recess in a bone. The stem has first and second faces each of which is substantially planar, wherein the first and second faces are inclined relative to one another about a first axis. In some embodiments, the first face is a lateral face and the second face is a medial face.

In some embodiments, when the implant is implanted, the first axis is aligned along a substantially superior-inferior orientation.

In some embodiments, the lateral face and the medial face are also inclined relative to one another about a second axis that is perpendicular to the first axis. In some embodiments, when the implant is implanted, the second axis is aligned along a substantially anterior-posterior orientation.

In some embodiments, the implant includes an anterior face and a posterior face. The anterior face and the posterior face each extend between the medial face and the lateral face. The anterior face and the posterior face are inclined relative to one another about a third axis that is perpendicular to the first axis and the second axis. In some embodiments, when the implant is implanted, the third axis extends in a substantially medial-lateral orientation.

In some embodiments, a method of planning removal of an implant from a patient includes receiving at least one image of the implant in the patient; identifying regions of trabecular bone, cortical bone, and bone void; and determining one or more paths for a cutting edge of a rotating tool relative to one or more surfaces of the implant. In some embodiments, the paths are configured to remove sufficient bone to allow removal of the implant while minimizing removal of cortical bone.

In some embodiments, the method includes identifying one or more incision locations for allowing entry of an elongated shaft of the rotating tool into the patient's anatomy without damaging neurovascular bundles, ligaments, or tendons. In some embodiments, determining the one or more paths includes selecting one or more paths through at least one bone void.

Although the devices, kits, systems, and methods have been described in terms of exemplary embodiments, they are not limited thereto. Rather, the appended claims should be construed broadly, to include other variants and embodiments of the devices, kits, systems, and methods, which may be made by those skilled in the art without departing from the scope and range of equivalents of the devices, kits, systems, and methods.

What is claimed is:

1. A rotatable cutting tool for removing bone, the tool comprising:
an elongated shaft having at least one cutting edge; and
a depth stop coupled to the elongated shaft, the depth stop extending outwardly from the elongated shaft, the depth stop in the form of at least one of a sphere and a truncated cone;
wherein the depth stop is configured to contact tissue of a patient or a burr guide to restrict a depth of insertion of the elongated shaft such that a depth of a tip of the rotatable cutting tool remains constant as the rotatable cutting tool is pivoted.

2. The tool of claim 1, wherein the depth stop is adjustable along a length of the elongated shaft that includes a plurality of stops, and wherein the depth stop is configured to engage one of the plurality of stops to locate the depth stop along the elongated shaft.

3. The tool of claim 2, wherein the depth stop comprises a collar that is adjustable along the length of the elongated shaft.

4. The tool of claim 3, wherein the depth stop further comprises a set screw engaged with the collar such that rotation of the set screw secures the collar in position along the elongated shaft.

5. The tool of claim 1, wherein the elongated shaft includes a cutting portion along which the at least one cutting edge extends and a non-cutting portion that does not contain a cutting edge, and wherein the depth stop is positioned along the non-cutting portion.

6. The tool of claim 5, wherein the depth stop is located along the non-cutting portion such that a first segment of the non-cutting portion is located between the depth stop and the cutting portion and a second segment of the non-cutting portion is located between the depth stop and an end of the tool.

7. A guide for a rotating tool, the guide comprising:
a body having:
a contact surface configured to facilitate locating the guide relative to a patient;
a first guide channel:
configured to receive a rotating tool for removing bone from the patient, configured to guide the rotating tool as the rotating tool is swept along a path,
including a first opening extending through the contact surface, and
including a second opening extending through a guide face that is spaced apart from the contact surface, the first opening being smaller than the second opening, and the second opening being an elongated opening such that the rotating tool can be pivoted when disposed within the first guide channel; and
a second guide channel, the first guide channel defining a first mid-plane, the second guide channel defining a second mid-plane, and the first and second mid-planes are non-parallel;
wherein a portion of the body is radio-opaque.

8. The guide of claim 7, wherein the guide face is configured to engage a depth stop of the rotating tool to control a depth of insertion of the rotating tool.

9. The guide of claim 8, wherein the guide face is curved such that the depth of a tip of the rotating tool remains constant as the rotating tool is pivoted in the first guide channel.

10. The guide of claim 7, wherein the first guide channel is curved such that sweeping the rotating tool within the first guide channel sweeps the rotating tool along a curved path.

11. The guide of claim 7, wherein spikes extend from the contact surface for securing the guide to the patient.

12. The guide of claim 7, wherein the first guide channel defines a path that corresponds to a profile of an implant.

13. The guide of claim 12, wherein the guide is configured to contact a portion of the implant to orient the guide.

14. The guide of claim 7, further comprising a sleeve coupled to the body, the sleeve configured to receive the rotating tool and to translate within the first guide channel.

15. The guide of claim 14, further comprising at least one pin extending from the sleeve, wherein the body includes at least one slot extending through the body and into the first guide channel, and the at least one slot is configured to receive the pin to guide movement of the sleeve within the first guide channel.

16. A system, comprising:
a rotating cutting tool comprising:
an elongated shaft having at least one cutting edge for removing bone from a patient,
a depth stop coupled to the elongated shaft, a depth stop in the form of at least one of a sphere and a truncated cone and configured to restrict a depth off insertion of the elongated shaft such that the depth of a tip of the rotating cutting tool remains constant as the rotating cutting tool is pivoted; and
a guide, the guide having a body including:
a contact surface configured to position the guide relative to the patient;
a first guide channel:
configured to receive at least a portion of the elongated shaft of the rotating cutting tool such that the rotating cutting tool is guided as the at least one cutting edge is swept along a path.

* * * * *